United States Patent [19]
Posti et al.

[11] Patent Number: 5,525,354
[45] Date of Patent: Jun. 11, 1996

[54] PHARMACEUTICAL PREPARATION AND PROCESS FOR ITS MANUFACTURE

[75] Inventors: Juhani Posti; Kirsi Katila, both of Turku; Pertti Rantala, Littoinen, all of Finland

[73] Assignee: Leiras OY, Turku, Finland

[21] Appl. No.: 318,650

[22] PCT Filed: Apr. 21, 1993

[86] PCT No.: PCT/FI93/00166

§ 371 Date: Dec. 12, 1994

§ 102(e) Date: Dec. 12, 1994

[87] PCT Pub. No.: WO93/21907

PCT Pub. Date: Nov. 11, 1993

[30] Foreign Application Priority Data

Apr. 24, 1992 [SE] Sweden .................................. 9201299

[51] Int. Cl.⁶ .............................. A61K 9/30; A61K 31/66
[52] U.S. Cl. ......................... 424/451; 424/452; 424/457; 424/458; 424/459; 424/461; 424/462; 424/463; 424/464; 424/465; 424/468; 424/469; 424/470; 424/474; 424/475; 424/479; 424/480; 424/482; 424/489; 424/490; 424/493; 424/494; 424/497; 424/499; 424/500; 424/501; 514/553; 514/578; 514/738

[58] Field of Search ..................... 424/451, 452, 424/457, 458, 459, 461, 462, 463, 464, 465, 468, 469, 470, 471, 472, 474, 475, 479, 480, 482, 489, 490, 493, 494, 497, 499, 500, 501; 514/553, 578, 738

[56] References Cited

U.S. PATENT DOCUMENTS 4,980,171  12/1990  Fels et al. .............................. 424/473

FOREIGN PATENT DOCUMENTS

0063014A3  10/1982  European Pat. Off. ..
0275468A1   7/1988  European Pat. Off. ..
0313845A1   5/1989  European Pat. Off. ..

*Primary Examiner*—Nathan M. Nutter

[57] ABSTRACT

In a pharmaceutical preparation for oral use containing a pharmacologically acceptable salt of a bisphosphonic acid, the improvement comprising: a drug delivery form of the preparation which is enteric coated with a film which dissolves at a pH-value of from 5 to 7.2.

9 Claims, No Drawings

PHARMACEUTICAL PREPARATION AND PROCESS FOR ITS MANUFACTURE

BACKGROUND OF THE INVENTION

The object of the present invention is a pharmaceutical preparation for oral use, especially a tablet, which as its active ingredient contains a pharmacologically acceptable salt of dichloromethylene bisphoshonic acid, i.e. a clodronate, especially disodium clodronate.

Dichloromethylene bisphosphonic acid, especially in the form of its salt, such as the disodium salt, is a known drug for example for the treatment of diseases relating to the calcium metabolism and to the sceletal system, such as to the metabolism of the bone, for example for osteoporosis.

Clodronate has previously been administered orally in the form of conventional compressed tablets or capsules. Such a tablet or capsule disintegrates in the stomach of the patient releasing the active agent, which in the acidic environment of the stomach is converted to the free acid form. As clodronic acid is poorly absorbed, the bioavailability of the active agent will be low, and consequently the required dosage level has to be increased. This in turn is a disadvantage as a large tablet has to be used, which is inconvenient for the patient and reduces patient compliance. Also a large dose increases the risk for side-effects.

SUMMARY OF THE INVENTION

According to the invention it has now been discovered that it is possible to achieve a substantially improved bioavailability if the active agent is prevented from being transformed into its acid form, that is, if it is allowed to pass the stomach region in unliberated form into the lower digestive tract to be released at a site thereof which is optimal from the point of view of the absorption of the active agent.

According to the invention it has now been discovered that the said objective is reached if the preparation is a drug delivery form which is enteric coated with a film which dissolves at a pH of from 5 to 7.2.

Preferably the film dissolves at a pH of from 5.0 to 6.5.

There is a number of film forming agents suitable for the purpose of the invention. Important from the point of view of the invention is that the agent used dissolves at the pH mentioned, i.e. at pH 5 to 7.2. These agents are known as such and there is a number of commercially available substances. Of such agents may be mentioned i.a. shellac, cellulose acetate phthalate (CAP) (e.g. Aquateric® by FMC Corporation), hydroxypropyl methylcellulose acetate succinate (HPMCAS, e.g. Aqoat® by ShinEtsu), hydroxypropyl methylcellulose phthalate (HPMCP, HP 50 and HP 55 by ShinEtsu), polyvinyl acetate phthalate (PVAP), cellulose acetate trimellitate (CAT, by e.g. Eastman Fine Chemicals), as well as various methacrylic acid derivatives (Eudragits by RöhmPharma).

The film forming agents are used dissolved either in suitable organic solvents (e.g. alcohols, chlorinated hydrocarbons, acetone etc), or in water, optionally in mixture with an organic solvent, and optionally using plasticizers, also known in the art, e.g. phthalic esters, citric esters, triacetin.

A preferred film forming agent to be used in the invention is hydroxypropyl methylcellulose phthalate, which is e.g. commercially available in forms that dissolve at pH 5 or alternatively pH 5.5.

The pharmaceutical preparation can be of any shape and form suitable to be provided with an enteric coating, representative examples being a tablet, granule, pellet, capsule or the like.

It has, according to the invention, surprisingly been discovered that the level of absorption of clodronate from a drug delivery form, which is enteric coated with a film forming agent which dissolves at the said pH of 5.0 to 7.2, is more than twice as high as from a corresponding drug delivery form which is uncoated, and even 4 to 5 times better than the absorption from a tablet suspended in water or from a sachet. This is be apparent from the absorption tests and their results presented later.

In the preparation according to the invention clodronate is used preferably as its disodium salt, either as the anhydrate or as a hydrate (tetrahydrate), the latter forming needle-shaped crystals of a size<100 μm. The preparation according to the invention may, in addition to the active agent, contain conventional additives, such as carriers, diluents, fillers, lubricants, disintegrating agents etc. These are known in the art. The amount of clodronate in the preparation can vary within wide limits, e.g. from 10 to 95% by weight, being typically 50 to 90% by weight. The film constitutes usually about 2 to 10% by weight of the total weight of the preparation, typically about 3 to 5% by weight. The exact amount and the thickness of the film are not critical, as long as the film is intact.

The invention also concerns a process for the preparation of the said oral preparation according to which a pharmacologically acceptable salt of dichloromethylene bisphosphonic acid is combined with a pharmacologically acceptable carrier or other additivies, whereafter the mixture obtained is formulated into a drug delivery form and coated to form a film which dissolves at a pH-value of from 5 to 7.2.

DETAILED DESCRIPTION

The preparation thus takes place by combining the active agent with per se known carrier and other additives and adjuvants. As a filler for example lactose, microcrystalline cellulose (e.g. Emcocel 90 M), mannitol and corn starch may be used. Also a disintegrating substance, such as croscarmellose sodium (Ac-Di-Sol), a binder, such as polyvidone (e.g. Kollidon K 30) and stearic acid may be used, which last mentioned substance may also function as a lubricant, as also magnesium stearate. As a lubricant also talc and colloidal silicon dioxide (e.g. Aerosil 200) may be used. When formulating the preparation, water and/or ethanol is used, typically as solvents for the binder in the granulation. The preparation is carried out using per se known tabletting, granulating or pelletization techniques.

The cores thus prepared are then coated and for this purpose any apparatus suitable for film coating may be used, such as Accela-Cota type of apparatus (Manesty) or apparatuses based on air suspension technique, e.g. Aeromatic or Glatt.

For this purpose the film forming agent is dissolved, depending on the agent, either in a suitable organic solvent, such as methanol, methylene chloride or acetone, or in water or e.g. a water-alcohol mixture, the alcohol typically being e.g. methanol, ethanol or isopropanol.

In the following the invention is illustrated by means of an example, which is in no way intended to be limiting.

EXAMPLE 1

For the preparation of a tablet according to the invention the following ingredients were used for the tablet core:

| | |
|---|---|
| Disodium clodronate anhydrate | 800.00 mg |
| Polyvidon | 30.00 mg |
| Croscarmellose sodium | 29.40 mg |
| Microcrystalline cellulose | 38.70 mg |
| Lactose | 119.91 mg |
| Stearic acid | 18.75 mg |
| Coll. anhydrous silicon dioxide | 20.00 mg |
| Talc | 34.00 mg |
| Magn. stearate | 9.24 mg |

In the first stage of the tablet preparation, the clodronate is granulated with polyvidon in a mixture of water and ethanol. The drug is wet granulated and sieved through a 1.5 mm sieve. The wet mass of granules is dried at about 40° C. to a suitable total moisture content of appr. 19%. The dried granules are then sieved on a 1.25 mm sieve. Thereafter the clodronate-polyvidon-granules are mixed with the colloidal silicon dioxide, Croscarmellose sodium and microcrystalline cellulose. The mixture is wetted with a solution of stearic acid and ethanol, wet-sieved and dried at +30° C. to a moisture content of appr. 18%. Thereafter the mass is dry-sifted through a 1.5 mm sieve. The remaining colloidal silicon dioxide as well as the talc, magnesium stearate and the lactose is added while mixing. Thereafter the mixture is formed into tablets in tabletting apparatus, using 9×21 mm punches to form tablets of a mean weight of 1.3 g (±5%).

The prepared tablets were then coated with a coating solution, the composition of which per table was

| | |
|---|---|
| Hydroxypropyl methyl-cellulose phthalate (HP 55) | 52.00 mg |
| Diethylphthalate | 7.80 mg |
| Ethanol | 516.60 mg |
| Purif. water | 135.70 mg |

The diethylphthalate is the plasticizer and the ethanol and the water form the evaporating part of the system. The "solids" content of the HPMCP-solution was about 9%.

The coating took place in an apparatus of Accela Cota-type under the following coating conditions.

Accela Cota 24"-coating apparatus (Ecco 40 DA-spray gun; Watson-Marlow peristaltic pump)

| | |
|---|---|
| Cores | 9 kg |
| Inlet air temp. | appr. +50° C. |
| Outlet air temp. | appr. +35° C. |
| Core temp. | appr. +30° C. |
| Injection speed | 30–20 rpm |
| Preheating time | appr. 10 min |
| Drum speed | appr. 8 rpm |
| Atomizing air pressure | 2.5 bar |

In the following test report the results of experiments are reported wherein the bioavailability of an enteric coated tablet according to the invention (Example 1) was compared to an uncoated, but otherwise to its composition identical clodronate tablet, as well as to that of a clodronate sachet formulation and a clodronate solution.

The composition of the sachet was:

| | |
|---|---|
| Disodium clodronate | 800.00 mg |
| Polyvidon | 50.00 mg |
| Aspartame | 50.00 mg |
| Arom. Passion | 62.50 mg |
| Mannitol | 87.50 mg |
| Spir. fort. | q.s. |
| Aq. purif. | q.s. |

METHOD

The panel consisted of 6 healthy volunteers, 3 women and 3 men, 24 to 28 years of age. Each subject received one 800 mg dose of clodronate sachet and one 800 mg enteric coated tablet of clodronate with 200 ml of water. All six subjects had participated in an earlier study wherein i.a. an uncoated tablet had been tested, and four of them had received a 800 mg clodronate tablet suspended in 200 ml of water. These data were used as historical controls for the present study. The interval between the studies was six months.

The study was of a balanced, randomized, two-period cross over design.

Fourteen (14) venous blood samples (10 ml each) were taken during each study period according to the following schedule: 0 (pre-drug), 0.25 (15 min), 0.5 (30 min), 0.75 (45 min), 1.0, 1.5, 2.0, 3.0, 4.0, 6.0, 8.0, 10.0, 12.0, and 24.0 hours following drug administration.

Urine was gathered as follows: In fractions of two hours up to 8.0 h (0.0–2.0 h, 2.0–4.0 h, 4.0–6.0 h and 6.0–8.0 h), of four hours up to 12.0 h (8.0–12.0 h) and of twelve hours up to 24.0 h (12.0–24.0 h).

Analysis of free, unmetabolized clodronate in serum was carried out by a gas chromatographic—mass spectrometric method. The detection limit of the method was 30 ng/ml and it was linear from 30 to 3000 ng/ml.

Detection of free, unmetabolized clodronate in urine was executed by a gas chromatographic method. The method was linear from 5 to 250 µg/ml.

The statistical analyses were carried out using Siphar program.

RESULTS

The $AUC_{0-24h}$ (area under curve) of the four clodronate formulations are presented in the following table:

| Delivery form | $AUC_{0-24h}$ (ng/ml*h) |
|---|---|
| Enteric tablet | |
| mean | 2478.60 |
| standard deviation (SD) | 1787.18 |
| Tablet | |
| mean | 1195.06 |
| SD | 930.45 |
| Sachet | |
| mean | 679.03 |
| SD | 360.22 |
| Susp. tablet | |
| mean | 564.78 |
| SD | 505.05 |

From the results in the table it clear that the $AUC_{0-24h}$ values for the four clodronate delivery forms, i.e. the enteric coated tablet tablet sachet and dissolved tablet differed significantly from each other. The bioavailability of the enteric coated tablet was approximately twice that of an ordinary tablet, and the bioavailability from the solution formulations (sachet and dissolved tablet) were about the half of that from the ordinary tablet.

We claim:

1. In a pharmaceutical preparation for oral use containing a pharmacologically acceptable salt of dichloromethylene bisphosphonic acid, the improvement comprising: a drug delivery form of the preparation which is enteric coated with a film which dissolves at a pH-value of from 5 to 7.2.

2. Preparation according to claim 1, wherein the film dissolves at a pH-value of 5.0 to 6.5.

3. Preparation according to claim 1, wherein the film is selected from the group consisting of cellulose acetate phthalate (CAP), hydroxypropyl methylcellulose acetate succinate (HPMCAS), hydroxypropyl methylcellulose phthalate (HPMCP), polyvinyl acetate phthalate (PVAP), cellulose acetate trimellitate (CAT), and metacrylic acid derivatives.

4. Preparation according to claim 1, wherein the drug delivery form is selected from the group consisting of a tablet, capsule, granule and pellet.

5. Preparation according to any one of the preceeding claims, wherein the active agent is the disodium salt of dichloromethylene bisphosphonic acid.

6. Process for the manufacture of a pharmaceutical preparation according to claim 1, wherein a pharmaceutically acceptable salt of dichloromethylene bisphosphonic acid is combined with a pharmacologically acceptable carrier or other adjuvants, the mixture obtained is made into a drug delivery form, which is coated with a film which dissolves at a pH-value of from 5 to 7.2.

7. Preparation of claim 3, wherein the film is hydroxypropyl methylcellulose phthalate.

8. Preparation of claim 4, wherein the drug delivery form is a tablet.

9. A dosage form of a bisphosphonic acid for ingestion by a patient first into a stomach and subsequently into an intestine of the patient comprising:

a core, said core having a pharmacologically acceptable salt of the bisphosphonic acid; and a film surrounding the core, said film dissolving at a pH of 5 to 7.2 and remaining substantially undissolved in the normal pH of the stomach such that the bisphosphonic acid remains surrounded by the film in the stomach, said film disintegrating in the presence of the intestine to release said salt of the bisphosphonic acid in the intestine.

* * * * *